United States Patent [19]

Gier et al.

[11] Patent Number: 4,602,112

[45] Date of Patent: Jul. 22, 1986

[54] ZEOLITE H-ZK-5 AS CATALYST FOR CONVERSION OF METHANOL AND AMMONIA TO DIMETHYLAMINE

[75] Inventors: Thurman E. Gier; Robert D. Shannon, both of Chadds Ford, Pa.; George C. Sonnichsen, Wilmington, Del.

[73] Assignee: E. I. Du Pont de Nemours and Company, Wilmington, Del.

[21] Appl. No.: 672,488

[22] Filed: Nov. 16, 1984

[51] Int. Cl.$^4$ .............................................. C07C 65/00
[52] U.S. Cl. ..................................... 564/474; 564/479
[58] Field of Search ................................ 564/474, 479

[56] References Cited

U.S. PATENT DOCUMENTS

| Re. 19,632 | 7/1935 | Arnold . | |
|---|---|---|---|
| 1,926,691 | 9/1933 | Swallen et al. . | |
| 1,992,935 | 3/1935 | Arnold . | |
| 2,349,222 | 5/1944 | Goshorn . | |
| 2,394,515 | 2/1946 | Goshorn . | |
| 2,394,516 | 2/1946 | Goshorn . | |
| 2,456,599 | 12/1948 | Smith . | |
| 3,278,598 | 10/1966 | Markiewitz . | |
| 3,384,667 | 5/1968 | Hamilton | 260/585 |
| 3,387,032 | 6/1968 | Leonard . | |
| 3,720,753 | 3/1973 | Robson | 423/329 |
| 4,082,805 | 4/1978 | Kaeding . | |
| 4,191,709 | 3/1980 | Parker et al. . | |
| 4,254,061 | 3/1981 | Weigert | 564/479 |
| 4,313,003 | 1/1982 | Weigert . | |
| 4,398,041 | 8/1983 | Cochran et al. | 564/479 |
| 4,434,300 | 2/1984 | Deeba et al. . | |
| 4,436,938 | 3/1984 | Tompsett | 564/474 |
| 4,485,261 | 11/1984 | Ashina et al. . | |

FOREIGN PATENT DOCUMENTS

| 0085408 | 10/1983 | European Pat. Off. . | |
|---|---|---|---|
| 56-53887 | 4/1981 | Japan . | |
| 49340 | 3/1983 | Japan | 564/479 |
| 422563 | 7/1933 | United Kingdom . | |

OTHER PUBLICATIONS

Restelli et al., *A. I. Ch. E. Journal,* 12:292 (1966).
Mochida et al., *Journal of Catalysis,* 82:313 (1983).

*Primary Examiner*—Charles F. Warren
*Assistant Examiner*—Joseph A. Boska

[57] ABSTRACT

A process is provided for producing dimethylamine comprising reacting methanol and/or dimethylether and ammonia in amounts sufficient to provide a carbon/nitrogen (C/N) ratio from about 0.2 to about 1.5, at a temperature from about 250° C. to about 450° C., in the presence of a catalytic amount of an acidic H-ZK-5 zeolite catalyst.

20 Claims, No Drawings

ZEOLITE H-ZK-5 AS CATALYST FOR CONVERSION OF METHANOL AND AMMONIA TO DIMETHYLAMINE

BACKGROUND OF THE INVENTION

This invention involves a process for making amines, particularly dimethylamine, in which methanol and/or dimethylether and ammonia are contacted in the presence of a selected zeolite catalyst.

Methylamines are generally prepared in industrial quantities by continuous reaction of methanol and ammonia in the presence of a silicaalumina catalyst. The reactants are typically combined in the vapor phase, at temperatures in the range of 300° to 500° C., and at elevated pressures. Trimethylamine is the principal component of the resulting product stream, accompanied by lesser amounts of monomethylamine an dimethylamine. From a commercial standpoint, the most valued product of the reaction is dimethylamine, in view of its widespread industrial use as a chemical intermediate. Accordingly, a major objective of those seeking to enhance the commercial efficiency of this process has been to improve overall yields of dimethylamine, and to a lesser extent, monomethylamine, relative to trimethylamine. Among the approaches taken to meet this objective are recycling of trimethylamine, adjustment of the ratio of methanol to ammonia reactants, and use of selected dehydrating or aminating catalyst species. Due to the commercial importance of the process, a rather extensive compendium of patents and other contributions to the technical literature has resulted. Representative references generally relevant to the field of the present invention are summarized in the following paragraphs.

Swallen, U.S. Pat. No. 1,926,691, discloses a process for producing dimethylamine by disproportionating monomethylamine over dehydrating or aminating catalysts such as alumina, silica, thoria, aluminum silicate or partially dehydrated aluminum trihydrate.

Arnold, U.S. Pat. No. 1,922,935, describes a process for catalytic synthesis of amines from alcohols and ammonia which employs as catalyst a dehydrating oxide, e.g., alumina, deposited on the surface of a porous, rigid gel, e.g., silica gel. Arnold, U.S. Pat. No. Re. 19,632, discloses a process improvement in which trimethylamine is introduced with the methanol and ammonia reactants to shift reaction equilibrium in favor of dimethylamine production.

Johnson, British Pat. No. 422,563, discloses a process for producing aliphatic amines involving heating an alcohol or ether under a pressure of more than about 50 atmospheres in the presence of a "catalyst capable of splitting off water" (e.g., alumina), with an excess of ammonia and optionally with addition of primary amine to the reaction mixture.

Goshorn, U.S. Pat. No. 2,349,222, discloses use of granular alumina coated with one or more oxides of nickel, cobalt, or chromium as a catalyst for alkylation of ammonia to produce alkyl amines. Goshorn, U.S. Pat. Nos. 2,394,515 and 2,394,516, discloses use as catalyst of an aluminum salt or oxide coated with silica and vanadium or molybdenum oxide.

Smith, U.S. Pat. No. 2,456,599, discloses a process improvement wherein water is added to a reactant feed mixture of methanol and ammonia to repress formation of tertiary amine in favor of primary and secondary amine.

Markiewitz, U.S. Pat. No. 3,278,598, discloses use of a rhodium, palladium, or ruthenium cocatalyst in conjunction with Raney metals to increase production of secondary amines from the reaction of alcohols and ammonia.

Rostelli et al., *A. I. Ch. E. Journal* 12:292 (1966) describe studies of transmethylation reactions of monomethylamine and dimethylamine over montmorillonite, a hydrated magnesium or calcium oxide-containing aluminosilicate having a porous lattice structure. For transmethylation of monomethylamine, this work indicated that reaction rate was directly proportional to reactant partial pressure, indicating that the rate-determining event is adsorption of reactant to the catalyst surface.

Hamilton, U.S. Pat. No. 3,384,667, describes alkylation of ammonia in the presence of a dehydrated crystalline aluminosilicate catalyst having pores of a diameter permitting absorption of primary and secondary, but not tertiary, amine products. Among the many catalysts disclosed by this patent are the natural zeolites ferrierite, chabazite, erionite, and mordenite.

Leonard, U.S. Pat. No. 3,387,032, discloses a process for reacting ammonia with methanol and/or dimethyl ether in the presence of a catalyst consisting of a silica gel base impregnated with 10–15% alumina which is first steam-deactivated and then treated with silver, rhenium, molybdenum, or cobalt ions to promote selectivity for dimethylamine.

Kaeding, U.S. Pat. No. 4,082,805, discloses use of a crystalline aluminosilicate or zeolite catalyst having the structure of ZSM-5, ZSM-11 or ZSM-21 in a process for producing amines by reaction of ammonia with $C_1$–$C_5$ alcohols at elevated temperatures and pressures.

Parker et al., U.S. Pat. No. 4,191,709, describe use of a hydrogen form of zeolite FU-1 or zeolite FU-1 in which some or all of the protons have been replaced by bivalent or trivalent cations.

Weigert, U.S. Pat. No. 4,254,061, discloses a process in which production of monomethylamine is enhanced by reacting methanol and ammonia in amounts sufficient to provide a C/N ratio of 0.5 to 1.5 over a catalyst selected from (a) mordenite wherein the primary cation is Li, Na, HNa having at least 2% Na by weight, K, Ca, Sr, Ba, Ce, Zn or Cr;

(b) ferrierite wherein the primary metal cation is Li, Na, K, Ca, Sr, Ba, Ce or Fe;

(c) erionite ore;

(d) calcium erionite; and (e) clinoptilolite ore, at a temperature of 250°–475° C. and a pressure of 7–7000 kPa, a contact time, normalized to 7 kPa, of 0.1 to 60 seconds and a methanol conversion of 15–95%.

Ashina et al., Japanese published Patent Application No. 56-53887, and Mochida et al., *Journal of Catalysis* 82:313 (1981), also disclose use of mordenite zeolites to enhance production of dimethylamine in closely related variants of the process disclosed by Weigert.

Weigert, U.S. Pat. No. 4,313,003, discloses an improved process for disproportionating monomethylamine to dimethylamine and ammonia, comprising passing monomethylamine over a crystalline aluminosilicate catalyst selected from (a) mordenite wherein the primary cation is Na, HNa having at least 2% Na, Mg, Ca, Sr or Ba;

(b) ferrierite wherein the primary metal cation is Na, K, Mg, Ca, Sr or Ba;
(c) clinoptilolite; and
(d) phillipsite, at a temperature of 250°–475° C. and a pressure of 7–7000 kPa, at a feed rate of 0.1–10 grams of monomethylamine per gram of catalyst per hour, at a monomethylamine conversion of 15–75%.

Cochran et al., U.S. Pat. No. 4,398,041, describe a process for converting $C_1$–$C_4$ alcohols to a non-equilibrium controlled distribution of primary, secondary, and tertiary alkylamines. The process disclosed involves passing a mixture of reactant alcohols and ammonia into a first conversion zone containing a "shape-selective" crystalline aluminosilicate catalyst having a pore size selective for mono- and disubstituted alkylamine products; dividing the resulting product stream; passing one portion of this product stream to a second conversion zone containing another catalyst having a different pore size distribution; and combining the remaining portion of the first product stream with the product stream of the second conversion zone to yield a non-equilibrium controlled product distribution. The zeolite catalysts disclosed by this reference include 5A zeolite, REY zeolite, H-chabazite-erionite, H-erionite, H-mordenite, and H-Y zeolite. Deeba et al., published European Patent Application No. 0085408, disclose a method for improving methanol conversion rates comprising reacting methanol and ammonia over a highly acidic dehydrated aluminosilicate catalyst having a silicon to aluminum ratio of at least 2.0 and manifesting microporous diffusivity for methylamines. Deeba et al., U.S. Pat. No. 4,434,300 disclose a method for improving methanol conversion rates in the reaction of methanol and ammonia to produce methylamines which comprises effecting the reaction in the presence of a macroporous, highly acidic aluminosilicate.

Tompsett, U.S. Pat. No. 4,436,938, discloses a process for making methylamines comprising reacting methanol and/or dimethyl ether over a binderless zeolite A catalyst, preferably a binderless zeolite 5A catalyst.

Currently, methylamines are produced using an adiabatic plug flow reactor. Although specific conditions do vary depending upon ammonia feed ratio and amount of product recycle, reactor inlet temperatures are generally run from about 310° C. to about 340° C., and outlet temperatures are preferably about 400° C. to about 430° C. The difference between inlet and outlet temperatures is due to exothermicity of the reaction and is moderated by recycling of ammonia and trimethylamine. The foregoing temperatures represent a compromise between increasing production rates at a given reactor size, which is favored at high reaction temperatures, and reducing catalyst deactivation, which is minimized at lower reaction temperatures. More active catalysts permit operation at lower reaction temperatures, increasing catalyst life and/or decreasing the need to recycle ammonia or trimethylamine.

As the foregoing discussion suggests, new process improvements which optimize dimethylamine yields while suppressing production of trimethylamine in this widely-practiced process are of significant interest to the chemical industry.

SUMMARY OF THE INVENTION

The present invention provides a process for producing dimethylamine comprising reacting methanol and/or dimethylether and ammonia in amounts sufficient to provide a carbon/nitrogen (C/N) ratio from about 0.2 to about 1.5, at a temperature from about 250° C. to about 450° C., in the presence of a catalytic amount of an acidic ZK-5 zeolite.

DETAILED DESCRIPTION OF THE INVENTION

Zeolites can be generically described as complex aluminosilicates characterized by a three-dimensional framework structure enclosing cavities occupied by ions and water molecules, all of which can move with significant freedom within the zeolite matrix. In commercially useful zeolites, water molecules can be removed from or replaced within the framework without destroying its geometry. Zeolites can be represented by the following formula:

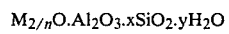

$$M_{2/n}O \cdot Al_2O_3 \cdot xSiO_2 \cdot yH_2O$$

wherein M is a cation of valence n, $x \geq 2$, and y is a number determined by the porosity and the hydration state of the zeolite, generally from 2 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Zeolite structure consists of corner linked tetrahedra with Al or Si atoms at centers of tetrahedra and oxygen atoms at corners. Such tetrahedra are combined in a well-defined repeating structure comprising various combinations of 4-, 6-, 8-, 10-, and 12-membered rings. The resulting framework consists of regular channels and cages, which impart a useful pore structure for catalysts. Pore dimensions are determined by the geometry of the aluminosilicate tetrahydra forming the zeolite channels or cages, with nominal openings of 2.6 Å for 6-rings, 4.0 Å for 8-rings, and 5.5 Å for 10-rings. Pore dimensions are critical to catalytic performance, since this zeolite characteristic determines whether reactant molecules can enter and product molecules can exit the zeolite framework. In practice, it has been observed that very slight decreases in ring dimensions can effectively hinder or block movement of particular reactants or products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as $Na^+$ or $K^+$, which are situated in or near 8-ring openings as well as 6-ring openings. Access is enhanced by divalent ions, such as $Ca^{2+}$, which are situated only in or near 6-rings. Thus KA and NaA exhibit effective pore openings of about 0.3 nm and 0.4 nm respectively, whereas CaA has an effective pore opening of 0.5 nm.

Useful references generally relating to zeolite structure and characterization include the following:

Meier et al., *Atlas of Zeolite Structure Types* (International Zeolite Assn. 1978);

Mumpton, "Natural Zeolites" in *Reviews in Mineralogy* 14:1 (1977);

Smith, "Origin and Structure of Zeolites" in *Zeolite Chemistry and Catalysis,* ACS Monograph 171 (American Chemical Society, 1976).

CHARACTERISTICS OF ZK-5 ZEOLITES

Zeolite ZK-5 is a synthetic zeolite first described by Robson, U.S. Pat. No. 3,720,753. The disclosure of this patent, which provides details regarding synthesis of the ZK-5 zeolites, is incorporated by reference herein. The structure of ZK-5 consists of truncated cuboctahedra linked by hexagonal prisms and enlarged double 8-rings with openings of 3.9 Å. ZK-5 zeolites can be characterized by the following formula:

$$(K,Cs)_{30}Al_{30}Si_{66}O_{192}\cdot 98H_2O.$$

The cationic species $K^+$ and $Cs^+$ present in ZK-5 zeolites can be exchanged for protons in a conventional ion exchange with $H^+$ or by conversion to an ammoniated form ($NH_4$-ZK-5) which is subsequently converted to the acid form by calcination at elevated temperatures.

Acid forms of zeolites can be prepared by a variety of techniques including ammonium exchange followed by calcination, direct exchange of alkali ions for protons using mineral acids or ion exchangers, and introduction of polyvalent ions (for a discussion of acid sites in zeolites, see Dwyer, "Zeolite Structure, Composition and Catalysis" in *Chemistry and Industry*, Apr. 2, 1984). The acid sites produced are generally believed to be of the Bronsted (proton donating) type or of the Lewis (electron pair accepting) type. Bronsted sites are generally produced by deammoniation at low temperatures, exchange with protons, or hydrolysis of polyvalent cations. Lewis sites are believed to arise from dehydroxylation of the H-zeolites or from the presence of polyvalent ions. In the acidic zeolite catalysts of the present invention, Bronsted and/or Lewis sites can be present.

Although pore dimensions of a given zeolite can be determined from X-ray studies of its crystal structure, this information is relatively expensive and laborious to obtain and does not necessarily indicate catalytic selectivity. However, pore accessibility can be determined simply and directly by obtaining sorption data using a probe molecule of appropriate size. Sorption measurements are capable of detecting pore blockage and particular molecular constraints which are not necessarily detected by X-ray studies of crystal structure.

Accordingly, a criterion based upon empirical observations of zeolite sorption characteristics have been devised in order to assess the utility of various small-pore zeolites as catalysts for conversion of methanol and ammonia to dimethylamine. This criterion, which is herein designated the geometric selectivity index for dimethylamine, or GSI, is defined as net sorption of methanol (MeOH) divided by net sorption of n-propanol (n-PrOH), each measured at 25° C. following 20 hours' exposure to sorbate vapor. Sorption is expressed in weight percent, e.g., grams sorbate per 100 grams zeolite.

Sorption measurements are made using an apparatus substantially analogous to that described by Landolt, *Anal. Chem.* 43:613 (1971). In a typical experiment, 0.4 to 1 g of zeolite is pressed at 300–1000 psi into a self-supporting cylinder, inserted into a preweighed sample holder, evacuated, heated to 425° C., cooled, and then weighed in the sample holder. A sample is then exposed to sorbate vapor in a sorption manifold at 10–50% of its vapor pressure at 25° C., removed from the sorption manifold, and weighed again to determine sorption.

Zeolites exhibiting little appreciable methanol sorption, for example, less than 3 g methanol per 100 g zeolite, generally possess little catalytic activity for producing methylamines from methanol and ammonia. Such zeolites include those with blocked channels or zeolites in which 6-ring systems are the sole path of molecular transport within the framework. Zeolites with appreciable isopropanol sorption, for example, more than 3 g per 100 g zeolite, generally are associated with high ratios of TMA to DMA production. Active zeolites with sorptions of methanol or ethanol of about 10–25 g per 100 g zeolite and little or no isopropanol sorption produce monomethylamine and dimethylamine selectivity versus trimethylamine.

For ZK-5 zeolites, increases in GSI correlate with increases in selectivity for dimethylamine. The catalysts employed in the process of the present invention are acidic ZK-5 zeolites, for example, H-ZK-5. Preferred catalysts are acidic ZK-5 zeolites exhibiting a GSI greater than about 2. The most preferred zeolite species for use in the process of the present invention are acidic ZK-5 zeolites having a GSI greater than about 3.

CATALYST PREPARATION

Zeolite ZK-5 is synthesized in a K-Cs form substantially according to the procedure disclosed in Robson, U.S. Pat. No. 3,720,753. In one method of preparing the H-form employed in the process of this invention, $K^+$ and $Cs^+$ ions are exchanged for $NH_4^+$ ions and the resulting $NH_4^+$ form deammoniated by calcination at 400° C. to 700° C. More extensive exchange produces lower Cs content, which results in higher DMA selectivity at low dimethylether (DME) production levels. Although ion exchange of ammonium for $K^+$ and $Cs^+$ ions may be incomplete in any given experiment, typically leaving 1–5 Cs ions per unit cell, the product of ion-exchange is referred to herein as $NH_4$-ZK-5 or ammoniated ZK-5. Similarly, although deammoniation of $NH_4$-ZK-5 may not result in complete conversion of all $NH_4^+$ sites to $H^+$ or other sites, particularly when a sample is calcined at lower temperatures, the resulting product is referred to herein as zeolite H-ZK-5.

Identification of zeolite Cs,K-ZK-5 is generally made by X-ray powder diffraction. The integrated intensities of the observed X-ray peaks can be used as a measure of zeolite crystallinity. High intensities indicate a highly crystalline product, while low intensities indicate less crystalline material. However, as crystallite size falls below about 50 nm, X-ray diffraction peaks broaden (H. P. Klug and L. E. Alexander, *X-Ray Diffraction Techniques*, Wiley-Interscience, New York, 1974). When crystallite size falls below about 2–6 nm, the peaks become so broad that they are difficult to detect by conventional analog recording spectrometers.

However, despite a lack of measurable X-ray peak intensity, such "X-ray amorphous" zeolite crystallites are capable of shape selective catalysis, as recently reported by Jacobs et al., *J. Chemical Society, Chemical Communications*, p. 591 (1981). For such crystallites, zeolite crystallinity is evident from infra-red spectra, sorption measurements, and catalytic shape selectivity. The acidic ZK-5 zeolites of this invention can be highly crystalline, poorly crystalline, or X-ray amorphous crystallites.

It has previously been established (Kerr, "Hydrogen Zeolite Y, Ultrastable Zeolite Y, and Aluminum-Deficient Zeolites", in *Molecular Sieves, Advances in Chemistry Series* 121:210 (American Chemical Society 1973)) that $NH_4$-zeolites deammoniated by deep-bed calcination techniques exhibit properties distinct from those of zeolites deammoniated by shallow-bed calcination techniques. Deep-bed calcination refers to combinations of bed geometry and calcination conditions, e.g., thick beds and/or slow flow of gas over zeolite, which do not result in a rapid removal of gaseous $H_2O$ and $NH_3$ from the heated zeolite. In contrast, shallow-bed calcination refers to bed geometries and conditions, e.g., shallow beds and rapid stripping of gases from the bed, which maximize removal of $H_2O$ and $NH_3$ from zeolite. As used herein, "deep-bed calcination" refers to calcination conducted under conditions wherein bed depth exceeds 3 mm and little or no gas flow is provided above the zeolite.

Clearly, a continuous gradation of calcination conditions can be arranged between extreme "deep-bed" conditions and extreme "shallow-bed" conditions. Accordingly, definitions regarding such conditions are by necessity somewhat arbitrary, and various equivalents to the conditions for calcination set forth below can be arranged. However, the definitions for calcination conditions set forth in Table I, below, apply throughout the specification.

TABLE I

Catalyst Calcination Conditions

| | Bed Type | | |
|---|---|---|---|
| | Shallow Bed | Quasi-Deep Bed | Deep Bed |
| Bed Thickness (mm) | ≦3 | >3 | >3 |
| Gas Flow Conditions | Rapid or continuous gas flow, vaccuum gas removal, or fluidized bed conditions maintained during calcination | Same as shallow bed calcination | Little or no gas flow during calcination |
| Temperature (°C.) | 450–750 | 450–750 | 450–650 (preferred; reduced DME production) |
| | 450–550 (preferred) | | 650–750 (greater DME production) |

Zeolite H-ZK-5 containing relatively large quantities of Cs, e.g. 4 Cs ions/unit cell, exhibits greater selectivity to dimethylamine when the $NH_4$-form is calcined under deep-bed conditions at higher temperatures and/or for longer times. Increased deammoniation temperatures, however, appear to be more effective than increased calcination periods in increasing selectivity for dimethylamine. However, when zeolite $NH_4$-ZK-5 containing relatively large quantities of Cs is calcined at high temperature (>650°) under deep-bed conditions, the resulting catalyst shows high levels of dimethylether production. When zeolite $NH_4$-ZK-5 containing smaller quantities of Cs, e.g. 1 Cs ion/unit cell, is calcined under either shallow-bed or deep-bed conditions, dimethylamine selectivities do not seem to be highly dependent on calcination temperature. Regardless of Cs content, deep-bed calcination conditions appear to be more effective in achieving high dimethylamine selectivities than shallow-bed calcination conditions.

Generally, calcination temperatures must be sufficiently high to convert substantially all $NH_4^+$ sites to $H^+$ or other acid sites, yet not high enough to render significant amounts of the zeolite amorphous. The presence of $NH_4^+$ in a given sample can be determined by infrared measurements. Excessive calcination can lead to collapse of zeolite crystalline structure and an amorphous state, which is to be distinguished from the "X-ray amorphous" zeolitic materials described above. The "X-ray amorphous" zeolites are obtained by limiting crystallization times, so that very small zeolite crystallites result. These crystallites exhibit characteristic zeolite selectivity, but permit rapid ingress of reactant molecules and egress of product molecules but to their small size.

Where deep-bed conditions are employed and DME production is undesirable, calcination temperatures of about 450° to 650° C. are preferred. If DME production can be tolerated, the upper limit for calcination temperature can be extended to about 750° C. Where shallow-bed conditions are employed, calcination temperatures of about 450°–550° C. are preferred.

PROCESS CONDITIONS

As previously noted, the process of the present invention comprises reacting methanol and/or dimethylether (DME) and ammonia, in amounts sufficient to provide a carbon/nitrogen (C/N) ratio from about 0.2 to about 1.5, in the presence of acidic zeolite ZK-5, at a temperature from about 250° C. to about 450° C. Reaction pressures can be varied from 1–1000 psi (7–7000 kPa) with a methanol/DME space time of 0.01 to 80 hours. The resulting conversion of methanol and/or DME to methylamines is generally in excess of 85% (on a mole basis) and selectivity (on a mole basis) to dimethylamine is generally greater than 40%. In addition, the selectivity to and yield of trimethylamine is suppressed. Thus, molar yields of dimethylamine generally exceed 40% and molar yields of trimethylamine generally are less than 30%, under the process conditions of the present invention.

The process variables to be monitored in practicing the process of the present invention include C/N ratio, temperature, pressure, and methanol/DME space time. The latter variable is calculated as the mass of catalyst divided by the mass flow rate of methanol introduced to a process reactor (mass catalyst/mass methanol+DME fed per hour).

Generally, if process temperatures are too low, low conversion of reactants to dimethylamine will result. On the other hand, if temperatures are excessively high, equilibrium conversions and catalyst deactivation can occur. Preferably, reaction temperatures are maintained between about 300° C. and 400° C. with lower temperatures within this range essentially preferred in order to minimize catalyst deactivation. At relatively low pressures, products must be refrigerated to condense them for further purification, adding cost to the overall process. However, excessively high pressures require costly thick-walled reaction vessels. Preferably, pressures are maintained at 10–500 psi (70–3000 kPa). Short methanol/DME space times result in low conversions and tend to favor the production of monomethylamine. Long methanol space times may result either in inefficient use of catalyst or production of an equilibrium distribution of the products at very high methanol/DME conversions. Generally, methanol/DME space times of 0.01–80 hours are satisfactory, with methanol/DME space times of 0.10–1.5 hours being preferred (corresponding to methanol/DME space velocities of 0.013–100 g of methanol+DME/g of catalyst/hour, preferably 0.67–10 g of methanol+DME/g of catalyst/hour).

The molar reactant ratio of methanol and/or dimethylether to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 and 1.5, and preferably from 0.5 to 1.2 in conducting the process of the present invention.

The efficiency of the process of the invention is measured by overall conversion of methanol and/or DME to methylamines, and by selectivity of dimethylamine production. For example, if methanol is used as the sole reactant, overall conversion is determined by comparison of the amount (in moles) of methanol in the product mixture, which is considered to be unconverted, to the amount in the reactant feed. Thus, overall conversion, in percent, is given by:

$$100 \left( 1 - \frac{\text{Moles MeOH in product}}{\text{Moles MeOH in feed}} \right)$$

Conversion of methanol to methylamines, in percent, is given by:

$$100 \left( 1 - \frac{\text{Moles MeOH in product} + 2(\text{Moles DME in Product})}{\text{Moles MeOH in Feed}} \right)$$

Conversion of methanol to monomethylamine (MMA) in percent, is given by:

$$100 \left( \frac{\text{Moles MMA}}{\text{Moles MeOH in feed}} \right)$$

Similarly, conversion of methanol to dimethylamine (DMA), in percent, is given by:

$$100 \left( \frac{2(\text{Moles DMA})}{\text{Moles MeOH in feed}} \right)$$

and conversion of methanol to trimethylamine (TMA), in percent, is given by:

$$100 \left( \frac{3(\text{Moles TMA})}{\text{Moles MeOH in feed}} \right)$$

Finally, selectivity to DMA is calculated by analysis of product composition. Thus, selectivity to DMA, in percent, is provided by the following expression:

$$100 \left( \frac{2[\text{DMA}]}{[\text{MMA}] + 2[\text{DMA}] + 3[\text{TMA}]} \right)$$

For efficient operation, the catalyst must be selective at high conversions (87–98%) and a C/N ratio of 0.5–1.2.

In practicing the process of the invention, the zeolite catalyst can be combined with another material resistant to the temperature and other conditions employed in the process. Such matrix materials include synthetic or natural substances such as clays, silica, and metal oxides.

Comparison of selectivities for different samples should be made at similar conversions since selectivity varies with conversion. At low conversions, MMA production is favored; at very high conversions, the reaction will approach an equilibrium distribution and thus result in increased TMA production.

The process of the present invention can be further understood by reference to the following Examples, wherein all temperatures are expressed in degrees Celsius (°C.) and all percentages are by weight unless otherwise indicated. In composition determinations, it was assumed that there were 192 oxygen atoms per unit cell. Analysis determined the relative amounts of the various cations present, and remaining positively-charged species were assumed to be hydrogen.

EXAMPLE 1

Zeolite H-ZK-5 was prepared by the following procedure. A mixture of 68 mL 4M $K_2AlO_2OH$ and 23 mL 50% CsOH was added to 126 mL of colloidal silica (Ludox®·AS-40) in a polypropylene container and heated to 100°. After two days at that temperature, 20 mL $H_2O$ were added, and the resulting mixture was transferred to a steam bath at 90° C. After 11 days on the steam bath, the resulting product was washed with $H_2O$ and then dried. An X-ray diffraction pattern obtained for this material was in agreement with that provided by the disclosure of Robson, U.S. Pat. No. 3,720,753, for (K,Cs)-ZK-5. Cubic cell dimension was determined to be a=1.867 nm. This product was slurried 3 times, for 16 hours each time, with a 20% $NH_4NO_3$ solution, and then washed, dried, and heated in an oven under deep-bed conditions for 16 hours at 500°. The resulting product, which was designated H-ZK-5, exhibited the following composition upon analysis:

$$H_{16.4}Cs_{3.9}K_{0.6}Al_{20.8}Si_{75.2}O_{192}.$$

Two grams of the resulting catalyst were placed in a stainless-steel U-tube reactor 0.125 in (0.32 cm) in diameter and about 12 in (30 cm) in length. First, the reactor was heated to reaction temperature in a fluidized sand bath. The reaction pressure was maintained at atmospheric pressure, 14.7 lbs.-in$^{-2}$ (101 kPa). Reactants methanol and ammonia were fed to a preheater at a molar ratio of about 1, vaporized, and then passed through the reactor into contact with the catalyst sample. The reaction temperature and flow rate of reactants methanol and ammonia are set forth in Table I, below. The reactor effluent was continuously analyzed by gas chromatography for ammonia, dimethylether (DME), methanol, water, and mono-, di-, and trimethylamine. The percentage conversions of methanol (overall), of methanol to methylamines (MA), and the percentage selectivities of conversion to each methylamine species are given in Table II, below. That portion of methanol converted to other than methylamines was converted to DME in this and all other Examples reported herein.

EXAMPLES 2-4

Examples 2 through 4 demonstrate use of H-ZK-5 zeolites as catalysts for production of dimethylamine and also demonstrate that higher calcination temperatures and longer calcination periods increase selectivity of H-ZK-5 zeolites for dimethylamine. However, yields of byproduct dimethylether also increase when H-ZK-5 catalysts are calcined for longer periods or at higher temperatures.

Zeolite (Cs, K)-ZK-5 was prepared substantially according to the procedure set forth in Example 3 of Robson, U.S. Pat. No. 3,720,753. An X-ray diffraction pattern obtained for the resulting product agreed with that indicated in that patent for (Cs,K)-ZK-5. A cubic cell dimension derived from this X-ray diffraction pattern was a=1.867 nm. $NH_4$-ZK-5 was prepared by contacting 50 g of the (Cs,K)-ZK-5 with a 10% $NH_4NO_3$ solution at 80° for three one-hour periods (with changes of the ammonium nitrate solution) followed by drying at 110°. The resulting material was divided into four samples, which were deammoniated under deep-bed conditions for 10 hours at at different temperatures. The calcination temperatures for the samples employed in Examples 2-4 were as follows: Example 2, 450°; Example 3, 500°; Example 4, 600°.

Each of the foregoing samples was then evaluated for catalytic performance by a procedure substantially similar to that described for Example 1. The results, which are displayed in Table II, below, illustrate the effects of deep-bed calcination temperature upon dimethylamine selectivity of H-ZK-5 zeolite catalysts.

Examples 2-4 also illustrate use of GSI measurements to predict catalytic performance of selected samples of H-ZK-5 zeolite. As previously noted, increased GSI can be correlated with increased dimethylamine selectivity for H-ZK-5 zeolites.

Sorption measurements employed in determining GSI were carried out substantially as previously described. The results appear in Table II, below.

dimethylamine and decreasing yields of byproduct dimethylether.

Zeolite (Cs,K)-ZK-5 was prepared substantially according to the procedure set forth in Example 3 of Robson, U.S. Pat. No. 3,720,753. Zeolite $NH_4$-ZK-5 was prepared by contacting 61 g of zeolite (Cs,K)-ZK-5 with a 10% $NH_4NO_3$ solution at 80° for twelve four-hour periods (with changes of the ammonium nitrate solution) followed by drying at 110°. The resulting material was divided into six samples, which were deammoniated under deep-bed and shallow-bed conditions. Samples deammoniated under shallow bed conditions were treated as follows. Individual samples, consisting of 5.0 g of $NH_4$-ZK-5, were spread out in an $Al_2O_3$ boat, passed into the hot zone of a belt furnace at 0.64 cm/min, and calcined for between 4 and 20 hours under a $N_2$ flow of 20 L/min. Infra-red spectra were then obtained. Absence of an absorption bed at 1400 $cm^{-1}$ indicated that substantially all $NH_4^+$ ions had decomposed, providing H-ZK-5 containing essentially no $NH_4^+$. The shallow-bed calcination conditions for the samples employed in Examples 5-7 were as follows: Example 5, 450° for 20 hr; Example 6, 500° for 10 hr; Example 7, 600° for 4 hr. The deep-bed calcination conditions for the samples employed in Examples 8-10 were as follows: Example 8, 450° for 10 hr; Example 9, 500° for 10 hr; Example 10, 600° for 10 hr. An X-ray diffraction pattern obtained for the sample used in Example 7 indicated that this sample was X-ray amorphous.

Each of the foregoing samples were then evaluated for catalytic performance by a procedure substantially similar to that described for Example 1. The results, which appear in Table II, illustrate the effects of calcination conditions and Cs content upon dimethylamine selectivity of zeolite H-ZK-5 catalysts.

Examples 8-10 also illustrate use of GSI measurements to predict catalytic performance of selected samples of zeolite H-ZK-5. As previously noted, increased GSI can be correlated with increased dimethylamine selectivity for zeolite H-ZK-5.

TABLE II

Comparison of GSI and Catalytic Performance of H-ZK-5 Zeolites Calcined Under Varying Conditions

| Example | #Cs/ Unit Cell | GSI | Calcination T °C. | Time (hr) | Reaction T °C. | Feed Flow (mL/hr) | MeOH Conv. (%) | MeOH— MA Conv. (%) | MeOH— DME Conv. (%) | Selectivity (%) MMA | DMA | TMA |
|---|---|---|---|---|---|---|---|---|---|---|---|---|
| \multicolumn{13}{c}{DEEP-BED CALCINATION} |
| 1 | 3.9 | — | 500 | 10 | 325 | 4 | 86 | 78 | 8 | 20 | 53 | 27 |
| 2 | 3.9 | 1.25 | 450 | 10 | 325 | 1 | 98 | 83 | 15 | 11 | 44 | 44 |
| 3 | 3.9 | 1.56 | 500 | 10 | 325 | 1 | 94 | 69 | 25 | 13 | 54 | 32 |
| 4 | 3.9 | 3.60 | 600 | 10 | 325 | 1 | 98 | 68 | 30 | 13 | 78 | 10 |
| \multicolumn{13}{c}{SHALLOW-BED CALCINATION} |
| 5 | 1.1 | — | 450 | 20 | 375 | 6 | 91 | 79 | 12 | 14 | 44 | 42 |
| 6 | 1.1 | — | 500 | 10 | 400 | 4 | 93 | 86 | 7 | 16 | 46 | 38 |
| 7 | 1.1 | — | 600 | 4 | 400 | 2 | 75 | 66 | 9 | 19 | 29 | 52 |
| \multicolumn{13}{c}{DEEP-BED CALCINATION} |
| 8 | 1.1 | 4.5 | 450 | 10 | 350 | 6 | 92 | 81 | 11 | 12 | 68 | 21 |
| 9 | 1.1 | 3.9 | 500 | 10 | 350 | 4 | 92 | 88 | 4 | 12 | 69 | 19 |
| 10 | 1.1 | 5.0 | 600 | 10 | 400 | 8 | 93 | 88 | 5 | 18 | 56 | 26 |

EXAMPLES 5-10

Examples 5-10 demonstrate use of H-ZK-5 zeolites as catalysts for production of dimethylamine. These examples also demonstrate that lower Cs contents and deep-bed calcination conditions are more effective than higher Cs contents and shallow-bed calcination conditions in increasing the selectivity of H-ZK-5 zeolites for

COMPARATIVE EXPERIMENTS A-E

Comparative Experiments A-E demonstrate that certain zeolites having ports bounded by 8 aluminosilicate tetrahedra, for example, erionite, and certain zeolites having ports bounded by 10 or 12 aluminosilicate tetrahedra, for example, ferrierite, silicalite, and zeolite Y, display little or no selectivity to dimethylamine when compared to the values attained at equilibrium for the reaction of methanol and ammonia. Similar results are obtained when an alumina-silica catalyst (91% $Al_2O_3$, 6.5% $SiO_2$) is employed. Comparison of the results of Comparative Experiments A, B, C and E with examples of the invention conducted at similar flow rates suggest that comparable conversions are obtained using acidic ZK-5 zeolites at temperatures 75° below those employed in the comparative examples.

COMPARATIVE EXPERIMENT A

Zeolite H-ferrierite was prepared by heating a sample of ferrierite (Zeolon ® 700, Norton Company) to 500° in flowing $N_2$ for 10 hours and then contacting the resulting sample three times, for one hour each time, with a 10% $NH_4NO_3$ solution at 80°. The resulting material was dried and heated by increasing the temperature 50° per hour to 500°, and then held at 500° for ten hours. The resulting sample of H-ferrierite was then cooled and evaluated for dimethylamine selectivity by a procedure substantially similar to that described in Example 1. The conditions employed and the results obtained are set forth in Table III, below.

COMPARATIVE EXPERIMENT B

Zeolite H-erionite was prepared from a sample of zeolite $NH_4$-erionite (Linde ® E-10) by a procedure substantially similar to that described for preparation of H-ferrierite in Comparative Experiment A. The resulting material was evaluated for dimethylamine selectivity substantially according to the procedure of Example 1. The results obtained are set forth in Table III, below.

COMPARATIVE EXPERIMENT C

Methanol and ammonia were passed over a catalyst consisting of 2 g of zeolite H-silicalite (S-115, Union Carbide Corporation) substantially as described in Example 1. The conditions and results are displayed in Table III. This material sorbed 12.5 g methanol and 12.5 g n-propanol per 100 g catalyst, providing a GSI of 1.

COMPARATIVE EXPERIMENT D 100 g of zeolite $NH_4$-Y (Linde LZY-82) was calcined in air by heating in 50° stepwise increments to 540°, and then held at 540° for about 10 hours. The resulting product, zeolite H-Y, was evaluated for dimethylamine selectivity by a procedure substantially similar to that described in Example 1. The conditions and results are set forth in Table III.

COMPARATIVE EXPERIMENT E

In a procedure substantially similar to that described in Example 1, methanol and ammonia were passed over a catalyst consisting of 2 g of silica-alumina (91% $Al_2O_3$, 6.5% $SiO_2$; Harshaw Chemical Co., Al-1602T). The conditions and results are displayed in Table III, below.

TABLE III

Methylamine Selectivities of Selected 10- and 12-Ring Zeolites and Silica-Alumina Catalysts

| Comparative Experiment | Catalyst | T (°C.) | Feed Flow (mL/hr) | MeOH Conv. (%) | MeOH—MA Conv. (%) | Selectivity (%) MMA | DMA | TMA |
|---|---|---|---|---|---|---|---|---|
| A | H—ferrierite | 400 | 0.5 | 94 | 90 | 13 | 28 | 59 |
| B | H—erionite- | 400 | 2 | 98 | 98 | 18 | 31 | 51 |
| C | H—silicalite | 400 | 4 | 97 | 92 | 9 | 22 | 69 |
| D | H—Y LZY-82 | 300 | 4 | 94 | 70 | 1 | 4 | 95 |
| E | Harshaw Al 1602 | 400 | 6 | 92 | 80 | 11 | 14 | 75 |
| | Equilibrium | 400 | | | | 10 | 22 | 68 |

What is claimed is:

1. A process for producing dimethylamine comprising reacting methanol and/or dimethylether and ammonia in amounts sufficient to provide a carbon/nitrogen (C/N) ratio from about 0.2 to about 1.5, at a temperature from about 250° C. to about 450° C., in the presence of a catalytic amount of an acidic ZK-5 zeolite catalyst.

2. A process according to claim 1, conducted at a pressure from 7 to 7000 kPa and at a reactant feed rate sufficient to provide a methanol/DME space time of 0.01 to 80 hours.

3. A process according to claim 2, wherein the temperature is from 300° C. to 400° C.

4. A process according to claim 3, wherein the pressure is from 70 to 3000 kPa, and the methanol/DME space time is from 0.10 to 1.5 hours.

5. A process according to claim 4, wherein the C/N ratio is from about 0.5 to about 1.2.

6. A process according to claim 5, wherein the zeolite catalyst is an acidic ZK-5 zeolite having a geometric selectivity index greater than about 2.

7. A process according to claim 6, wherein the zeolite catalyst is an acidic ZK-5 zeolite having a geometric selectivity index greater than about 3.

8. A process according to claim 5, wherein the zeolite catalyst is an acidic ZK-5 zeolite prepared by calcination of an ammoniated ZK-5 zeolite at a temperature between 450° C. and 750° C.

9. A process according to claim 8, wherein the zeolite catalyst is an acidic ZK-5 zeolite prepared by calcination of an ammoniated ZK-5 zeolite under deep bed conditions at a temperature between 450° C. and 650° C.

10. A process according to claim 8, wherein the zeolite catalyst is an acidic zeolite prepared by calcination of an ammoniated ZK-5 zeolite under shallow-bed conditions at a temperature between 450° C. and 550° C.

11. A process according to claim 1, wherein the zeolite catalyst is an H-ZK-5 zeolite.

12. A process according to claim 2, wherein the zeolite catalyst is an H-ZK-5 zeolite.

13. A process according to claim 3, wherein the zeolite catalyst is an H-ZK-5 zeolite.

14. A process according to claim 4, wherein the zeolite catalyst is an H-ZK-5 zeolite.

15. A process according to claim 5, wherein the zeolite catalyst is an H-ZK-5 zeolite.

16. A process according to claim 6, wherein the zeolite catalyst is an H-ZK-5 zeolite.

17. A process according to claim 7, wherein the zeolite catalyst is an H-ZK-5 zeolite.

18. A process according to claim 8, wherein the zeolite catalyst is an H-ZK-5 zeolite.

19. A process according to claim 9, wherein the zeolite catalyst is an H-ZK-5 zeolite.

20. A process according to claim 10, wherein the zeolite catalyst is an H-ZK-5 zeolite.

* * * * *